United States Patent [19]

Zayek

[11] Patent Number: 5,042,939

[45] Date of Patent: Aug. 27, 1991

[54] LASER SCANNING TYPE EYE FUNDUS CAMERA

[75] Inventor: François Zayek, Buffalo Grove, Ill.

[73] Assignee: Topcon Corporation, Tokyo, Japan

[21] Appl. No.: 436,872

[22] Filed: Nov. 16, 1989

[51] Int. Cl.⁵ .............................................. A61B 3/10
[52] U.S. Cl. .................................. 351/206; 351/205; 351/221
[58] Field of Search ............... 351/205, 206, 211, 221; 354/62

[56] References Cited

U.S. PATENT DOCUMENTS 4,781,453 11/1988 Kobayashi ........................ 351/206

Primary Examiner—Rodney B. Bovernick
Attorney, Agent, or Firm—Finnegan, Henderson, Farabow, Garrett & Dunner

[57] ABSTRACT

A laser scanning type eye fundus camera is designed such that retina photographing for one frame is perofrmed alternately with two laser beams having two wavelengths among three laser beams wavelengths of the primary three colors and with one laser beam including the remaining one wavelength to obtain a retina image composed of the wavelengths of the respective primary colors which are combined to obtain one color retina image.

12 Claims, 7 Drawing Sheets

LASER SCANNING TYPE EYE FUNDUS CAMERA

BACKGROUND OF THE INVENTION

1. Field of the Invention

This invention relates to a laser scanning type eye fundus camera for scan projecting a laser beam onto the retina of an eye to be tested and receiving a reflected beam from the retina through a light receiving element and then color photographing the retina in accordance with a signal coming from the light receiving element.

2. Description of the Related Art

Heretofore, an illuminating light of somewhat strong (or intensified) energy has been used for projecting the same to the retina of an eye to be tested in order to photograph a retina using a conventional eye fundus camera.

The test according to this conventional method was painful to the patient both physically and mentally.

In recent years, in order to diminish this burden or pain and enhance the safety of the testing, there was proposed a laser scanning type eye fundus camera in which a laser beam is scan projected to the retina so that a strong (or intensified) energy would not be irradiated to a particular part for a long period of time. Moreover, as a color photograph obtained by illuminating the retina with a white light is useful in ordinary eye fundus testing, there has been contemplated a laser scanning type eye fundus camera by which a color photograph can be taken.

As such a laser scanning type eye fundus camera which is capable of color photographing, there is one disclosed, for example, in U.S. Pat. No. 4,781,453. In this laser scanning type eye fundus camera, the retina is photographed for each frame using a laser beam of various wavelengths in the four colors of R, G, B and Y, and retina images obtained by respective wavelengths are combined to obtain one color retina image.

However, when the retina is to be photographed for each frame in sequence using four kinds of laser beams which have different wavelengths, it takes a long period of time to obtain one color retina image. In such a long period of time, there is a problem that the retina image may be changed due to movement of the eye to be tested. Therefore, it becomes difficult to obtain a clear retina image because there occurs a slippage of the respective images when such images of various wavelengths are combined.

SUMMARY OF THE INVENTION

It is therefore an object of the present invention to provide a laser scanning type eye fundus camera which is capable of color photographing in a shorter period of time than the above-mentioned conventional eye fundus camera.

In order to achieve the above-mentioned object, the present invention includes laser beam generating means for generating laser beams having wavelengths of three primary colors;

a scanning optical system for scan projecting the laser beams to the retina of an eye to be tested;

switch means for selectively switching laser beams of various wavelengths coming from said laser beam generating means and guiding the same to said scanning optical system;

control means for controlling said switch means so as to selectively switch at least two laser beams among said three laser beams and permitting said scanning optical system to scan project one frame portion of such selected laser beams to the retina of the eye and also permitting said scanning optical system to scan project one frame portion of two laser beams or less including the remaining one among said three laser beams to the retina of the eye; a light receiving optical system for taking out a reflected light from the retina of the eye;

first light receiving means for receiving reflected light having two wavelengths among said wavelengths of said three primary colors which are guided by said light receiving optical system; second light receiving means for receiving a reflected light having the remaining one wavelength among said wavelengths of said three primary colors which is guided by said light receiving optical system; and image processing means for composing said various primary colors in accordance with output from said light receiving means in order to form a single color retina image.

These and other objects, features and advantages of the present invention will be well appreciated upon reading of the following description of the invention when taken in conjunction with the attached drawings with the understanding that some modifications, variations and changes of the same could be made by the skilled person in the art to which the invention pertains without departing from the spirit of the invention or the scope of claims appended hereto.

BRIEF DESCRIPTION OF THE ATTACHED DRAWINGS

DESCRIPTION OF THE PREFERRED EMBODIMENT

The embodiment of the present invention will be described hereinafter with reference to the drawings. FIGS. 1 through 5 show a first embodiment of the present invention.

Figure 1:
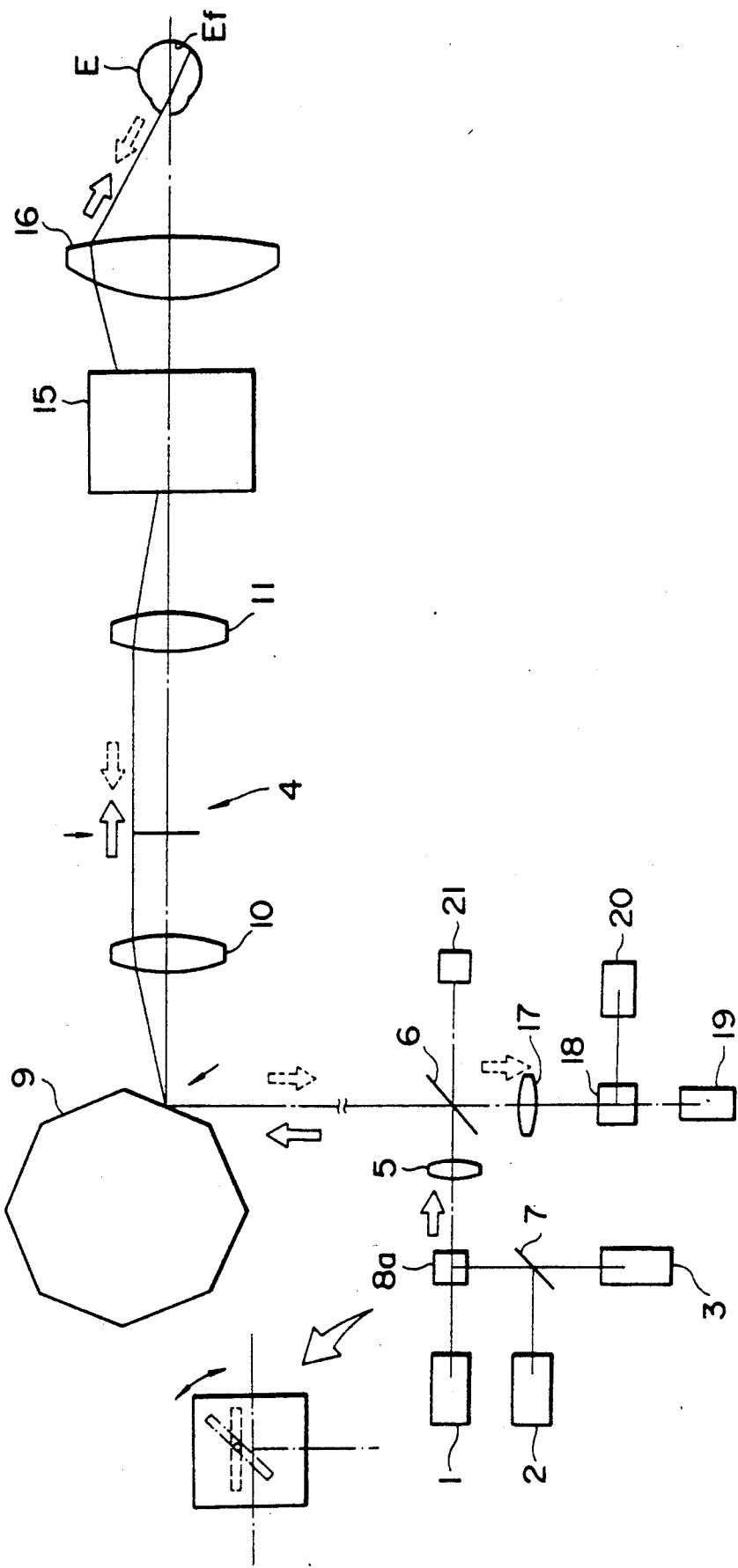
FIG. 1 is a plan view showing an arrangement of an optical systems of a laser scanning type eye fundus camera according to the present invention.

In FIG. 1, a laser scanning type eye fundus camera has first, second and third lasers 1, 2 and 3 (laser generating means) for generating laser beams having wavelengths of three primary colors, i.e., B (Blue), G (Green) and R (Red). The lasers 1, 2 and 3 may include a laser emitting diode or the like. Laser beams generated by the lasers 1, 2, 3 are made incident to the scanning optical system 4. In this case, a blue laser beam generated by the laser 1 is made incident to a scanning optical system 4 through a lens 5 and a half mirror 6 as a beam splitting means. Similarly, a green laser beam generated by the laser 2 is made incident to the scanning optical system 4 through a dichroic mirror 7, a rotating mirror 8a of an optical path switch device 8 (optical path switch means), the lens 5, and the half mirror 6. Likewise, a red laser beam generated by the laser 3 is made incident to the scanning type optical system through the rotating mirror 8a of the optical path switch device 8 (optical path switch means), the lens 5, and the half mirror 6 after transmitting through the dichroic mirror 7.

The dichroic mirror 7 is provided with a coating material so that a laser beam of a green wavelength is reflected and a laser beam of a red wavelength is permitted to transmit. Accordingly, the rotating mirror 8a can be removably inserted into the optical path as will be described afterward. When the rotating mirror 8a is removed from the optical path, the blue laser beam is guided to the scanning optical system 4. On the other hand, when the rotating mirror 8a is inserted into the optical path 4, the green and red laser beams are guided to the scanning optical system 4.

Figure 2:
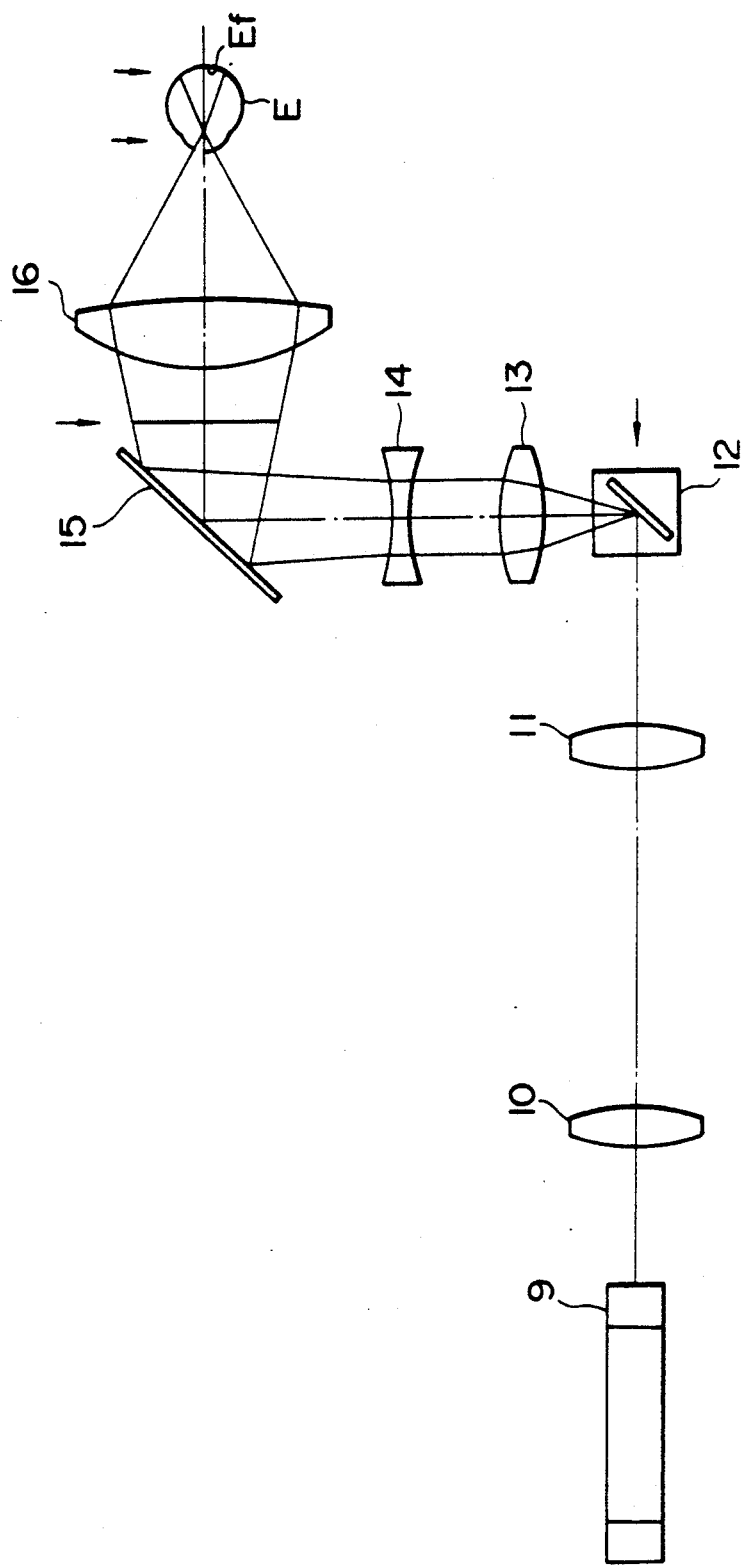
FIG. 2 is a schematic side view showing the arrangement of FIG. 1.

This scanning optical system 4, as shown in FIGS. 1 and 2, includes a polygonal scanner 9 for horizontally scanning a laser beam, relay lenses 10, 11 commonly used as a variable lens, a galvano scanner 12 for changing the horizontal scanning position of the polygonal scanner 9 to a vertical direction, a relay lens 13, a focus lens, a reflecting mirror 15, an objective lens 16, etc. Such scanning optical system 4 scan projects the laser beams from the lasers 1, 2 and 3 to the retina Ef of the eye to be tested in accordance with the operation of the scanners 9 and 12 to illuminate the retina Ef. The scanning range of the retina by the scanning optical system 4 can be changed to 20°~60° by the relay lens.

The reflected light from this retina Ef can be recieved through the light receiving optical system 4. This light receiving optical system includes the scanning optical system 4, the half mirror 6, a lens 17 and a dichroic mirror 18. The dichroic mirror 18 has such characteristics as to reflect the red light and permit the green and blue light to transmit. The reflected light received by this light receiving optical system and permitted to transmit through the dichroic mirror 18 is made incident to a light receiving device 19, such as P.M.T. (photomultiplier). The light reflected by this dichroic mirror 18 is made incident to a light receiving device 20 such as P.M.T. (photomultiplier), etc. Accordingly, when the reflected laser beams of blue, green and red colors reflected by the retina Ef are recieved through the light receiving optical system, the reflected laser beams of blue and green colors are permitted to transmit through the dichroic mirror 18 and input into the light receiving device 19. On the other hand, the reflected laser beam of the red wavelength is reflected by the dichroic mirror 18 and input into the light receiving device 20.

Also, a portion of the laser beams coming from the lasers 1, 2 and 3, is permitted to transmit through the half mirror 16 and made incident to a light receiving element 21 as a reference light receiving device.

Figure 3:
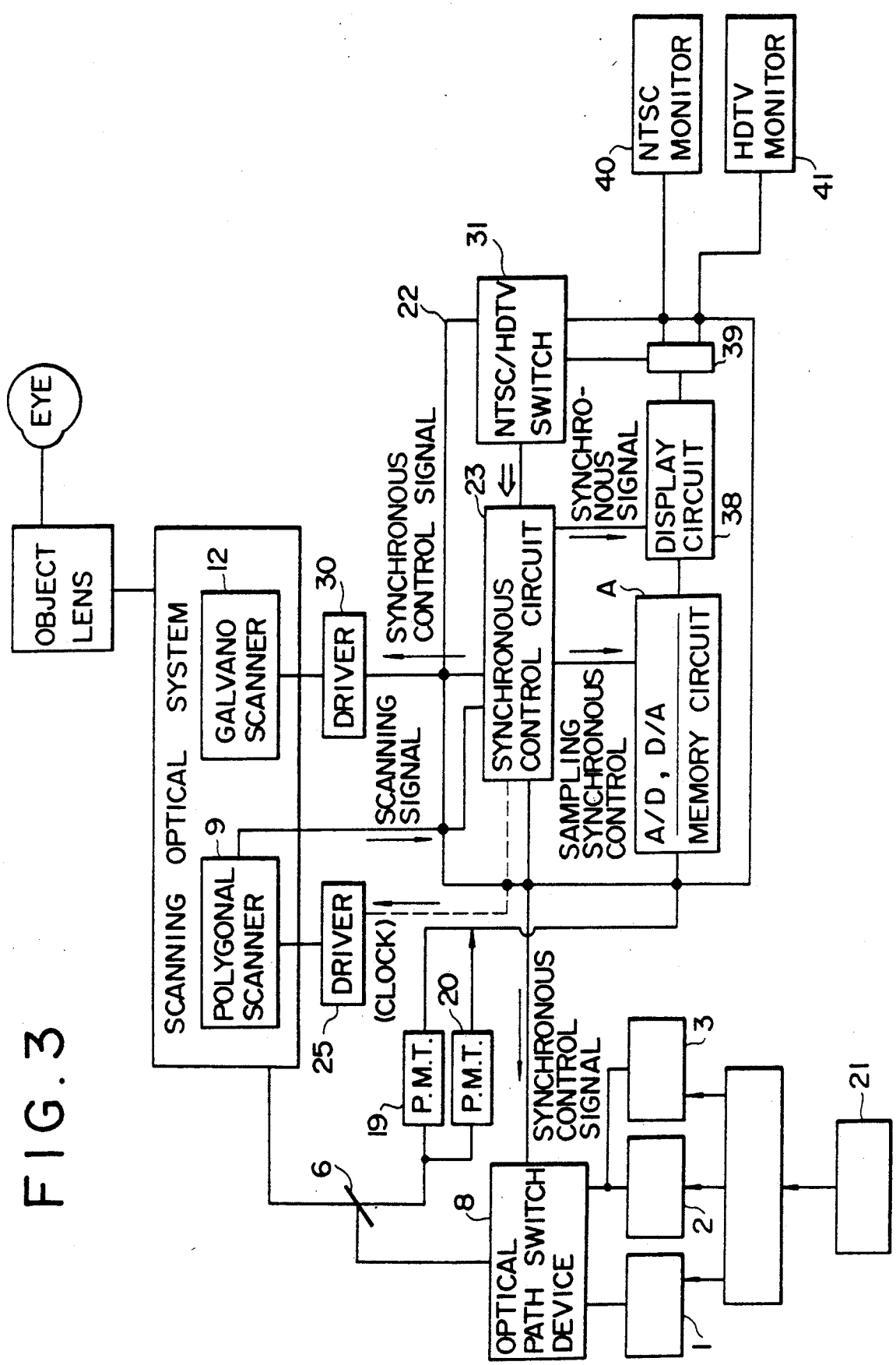
FIG. 3 is a control circuit diagram of a laser scanning type eye fundus camera shown in FIG. 2.
Figure 4:
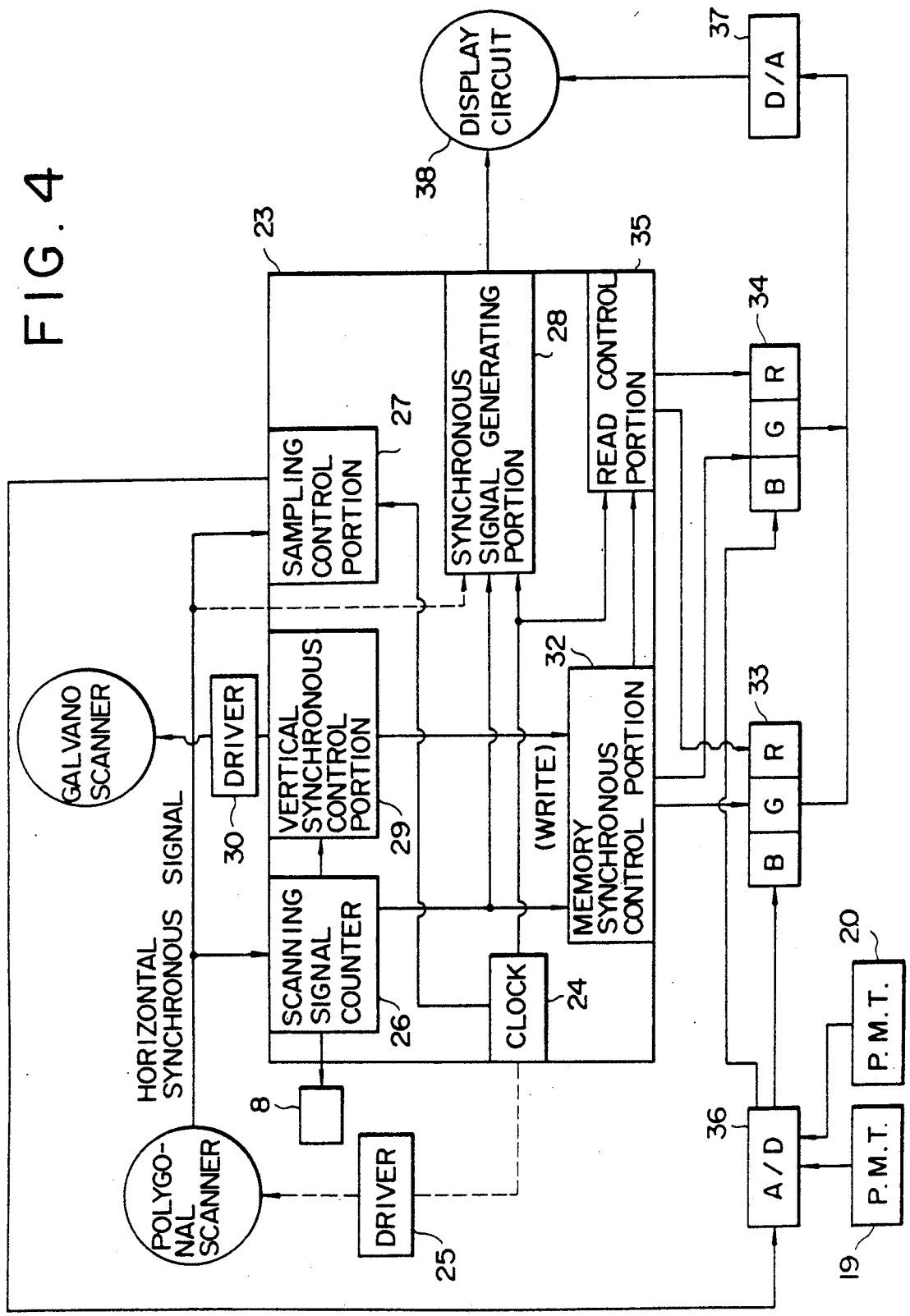
FIG. 4 is a detailed view of a synchronous control circuit shown in FIG. 3.

The mirror 8a, the polygonal scanner 9 and the galvano scanner 12 are drive controlled by a control circuit shown in FIG. 3. This control circuit 22' and its operation will now be described with reference to FIGS. 1 through 5.

Upon actuation of the control circuit 22, the polygonal scanner 9 is rotated at a high speed rate in accordance with a signal from a clock oscillator 24 of a synchronous control circuit 23 through a driver 25. When the laser beams are generated from the lasers 1, 2 and 3, in the foregoing state, the polygonal scanner 9 of the scanning optical system 4 horizontally scans the laser beams to the retina Ef by the number of reflecting surfaces every time the polygonal scanner 9 makes one rotation. On the other hand, the polygonal scanner 9 outputs a horizontal synchronous signal every time the laser beam has made one horizontal scanning to the retina Ef as described. This horizontal synchronous signal is input into a scanning signal counter 26, a sampling control portion 27, and a synchronous signal generating portion 28. A clock signal is input into the sampling control portion 27 and the synchronous signal generating portion 28 from the clock oscillator 24.

The scanning signal counter 26 counts the horizontal synchronous signal coming from the polygonal scanner 9 and inputs a scanning position change signal into a vertical synchronous control portion 29 every time the horizontal synchronous signal is input. The vertical synchronous control portion 29 outputs a vertical synchronous signal upon input of this scanning position change signal in order to cause a driver 30 to rotate the galvano scanner 12 by a predetermined angle to displace the horizontal scanning position downward by a predetermined pitch. Also, when all of the lines for one frame portion are scanned, a one frame scanning end signal is input into the vertical synchronous signal control portion 29 from the scanning signal counter 26 and an optical path switch signal is input into a mirror pivot driving means, such as a solenoid, of the optical path switch device 8.

By this, the vertical synchronous control portion 29 returns the galvano scanner 12 to the original scanning portion. On the other hand, the optical path switch device 8 is actuated by the optical path switch signal. When the mirror 8a of this optical path switch device 8 is inserted into the optical path, the mirror 8a is taken out of the optical path, whereas when the mirror 8a is removed out of the optical path, the mirror 8a is inserted into the optical path. A switching state of this mirror 8a is maintained until the next signal is input.

This scanning number is different depending on the switching state of a NTSC/HDTV switch 31. That is, when the NTSC/HDTV switch 31 is at the NTSC position, the polygonal scanner 9 is scan driven at 15.75 KHz and the galvano scanner 12 is driven at 30 Hz, and the number of the scanning lines becomes 525 for one frame portion. On the other hand, when the NTSC/HDTV switch 31 is at the HDTV side, the polygonal scanner 9 is driven at 15.75 KHz and the galvano scanner 12 is scan driven at 15 Hz, and the number of the scanning lines become 1050 for one frame portion. As the HDTV monitor has scanning lines of 1125 in the number, the speed is changed slightly when reading and displayed. Owing to the foregoing construction, a high resolution image can be photographed by scan driving at a comparatively low speed according to necessity.

On the other hand, the vertical switch signal and one frame scanning end signal are input into a memory synchronous control portion 32 and the synchronous signal generating portion 28 from the scanning signal counter 26, and the vertical synchronous signal is input into the memory synchronous control portion 32 from the vertical synchronous control portion 29. Synchronous signals are input into first and second memories 33 and 34 and a reading control portion 35 from this memory synchronous control portion 32. Similarly, control signals are input into the memories 33 and 34 from the reading control portion 35.

Also, output signals are input into the memories 33 and 34 from the light receiving devices 19 and 20 through an A/D converter 36. This A/D converter 36 is controlled by the sampling control portion 29 and output signals are input into the memories 33 and 34 from the light receiving devices 19 and 20. This input timing is performed every time a laser beam spot to be scanned to the retina Ef is moved for one portion.

Such spot quantity (i.e. an image information signal) for each spot is stored in sequence at predetermined addresses of the memory 33 by the memory synchronous control portion 32 every time one horizontal scanning is effected. That is, when the mirror 8a is removed out of the optical path, a blue reflected laser beam from the retina Ef is stored in sequence in a predetermined address of a memory portion B of the memory 33 by the memory synchronous control portion 32 every time one horizontal scanning is effected. When a memory construction of image information signals for one frame portion has been built up in the memory portion B and the mirror 8a has been inserted into the optical path, a green reflected laser beam from the retina Ef is stored in sequence in a predetermined address of a memory portion G of the memory 33 by the memory synchronous control portion 32 every time one horizontal scanning is effected and a red reflected laser beam from the retina Ef is stored in sequence in a predetermined address of a memory portion R of the memory 33 by the memory synchronous control portion 32 every time one horizontal scanning is effected. As a result, a memory construction for one frame portion is built up in the memory portions G and R. The memory storage for the memory portions G and R is completed in one frame scanning time period.

When a memory action to this frame memory 33 has been finished, a memory storage for the frame memory 34 is performed in the same manner. Such memory storage for the memories 33 and 34 is repeated.

When a storage operation to the memory 33 has been finished and a storage operation to the memory 34 is started, image information of the various memory portions B, G and R of the memory 33 is output by a read control portion. Similarly, when a storage operation to the memory 34 has been finished and a storage operation to the memory 33 is started, image information of the various memory portions B, G and R of the memory 34 is output by the read control portion. The image information of B, G and R output from the memories 33 or 34 is input into a display circuit 38 through a D/A converter 37. This display circuit 38 composes one color retina image from the image information of B, G and R. The A/D, D/A and memory circuit A of FIG. 3 include the memories 33 and 34, A/D converter, D/A converted, and other corresponding elements shown in FIG. 4.

The image signal is then input into an NTSC monitor 40 or an HDTV monitor 41 through a switch circuit 31. A synchronous signal is input into the display circuit 38 from the synchronous signal generating portion 28, and a signal is input into the switch circuit from the NTSC/HDTV switch 31.

Also, when laser beams emitted from the lasers 1, 2, and 3 are made incident to the scanning optical system 4, the laser beams are detected by the light receiving device 21. An output from the light receiving device 21 is input into a light quantity control portion to control the lasers 1, 2, and 3 to make the laser light quantity constant. The respective outputs of the lasers 1, 2, and 3 are set such that when an image of the various wavelengths is composed, it becomes white in color of course, the sensitivity of the light receiving element must be taken into consideration.

Figure 6:
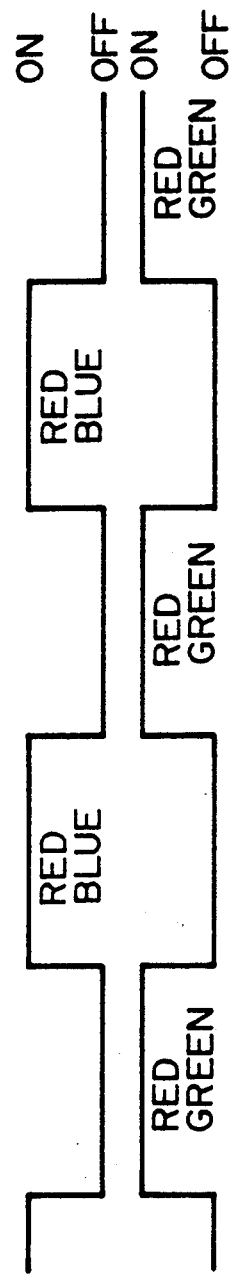
FIG. 6 is an explanatory view showing another example of photographing patterns of the laser scanning type eye fundus camera shown in FIGS. 1 through 4.

In the above-mentioned embodiment, retina photographing for one frame is performed with a laser beam of one wavelength within B, G and R and retina photographing for the next one frame portion is performed with laser beams of the other two wavelengths to obtain a retina image of wavelengths of B, G and R. By composing the various images obtained, one color retina image is obtained. However, the present invention is not necessarily so limited. For example, as shown in FIG. 6, it can be designed such that retina photographing for one frame is performed with two wavelengths of R and G and retina photographing for one frame is performed with laser beams of two wavelengths of R and B to obtain a retina image of B, G and R. By composing the various images, one color retina image may be obtained. In this case, since retina reflectance is high in R, the overlapping accuracy becomes good when images for two frames are composed and therefore, a clear image can be obtained.

Figure 5:
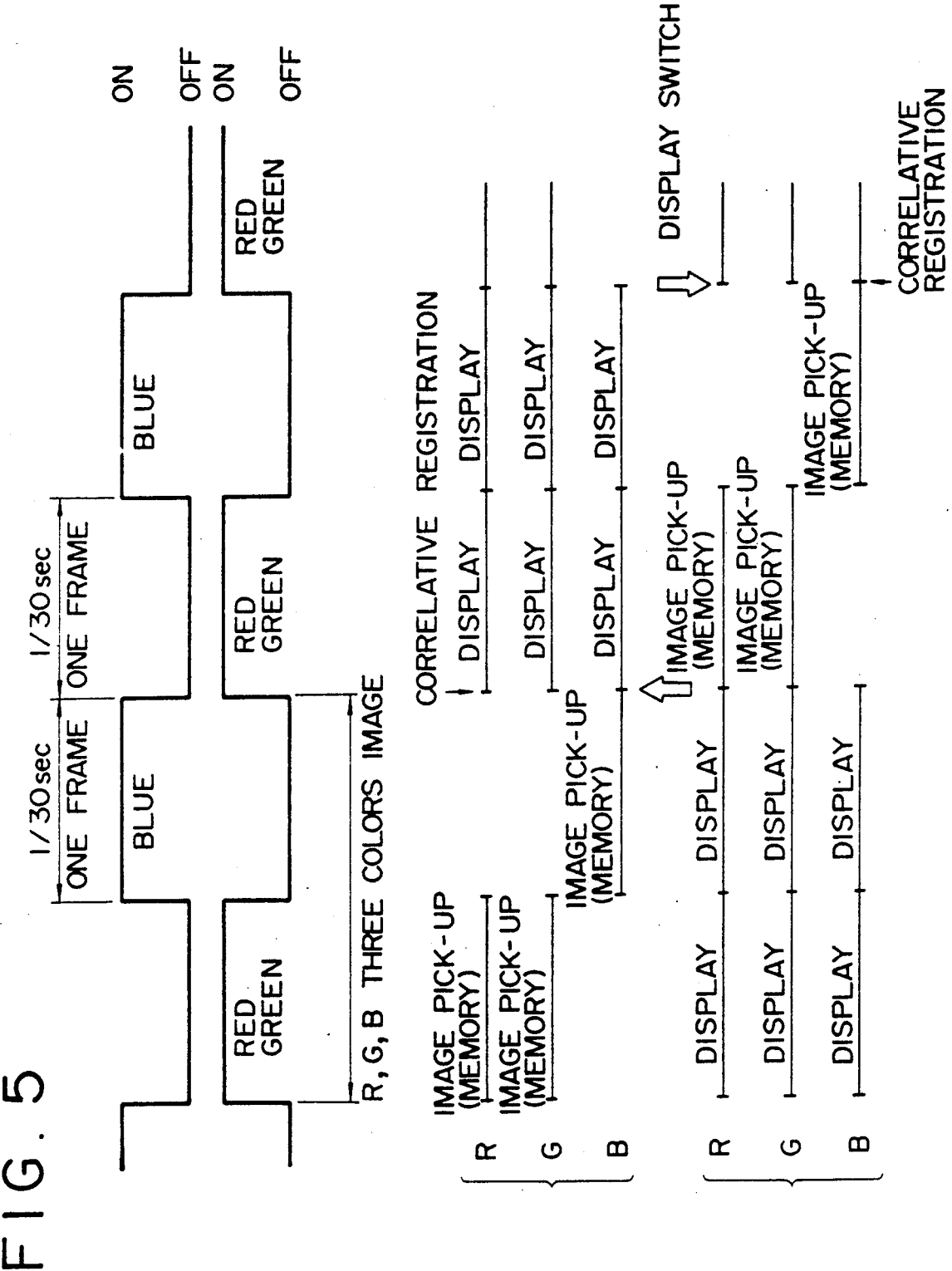
FIG. 5 is an explanatory view showing photographing patterns of the laser scanning type eye fundus camera shown in FIGS. 1 through 4.

Accordingly, the retina photographing and the monitor reproduction by the memories 33 and 34 are alternatively performed as shown by the timing diagram in FIG. 5.

Figure 7:
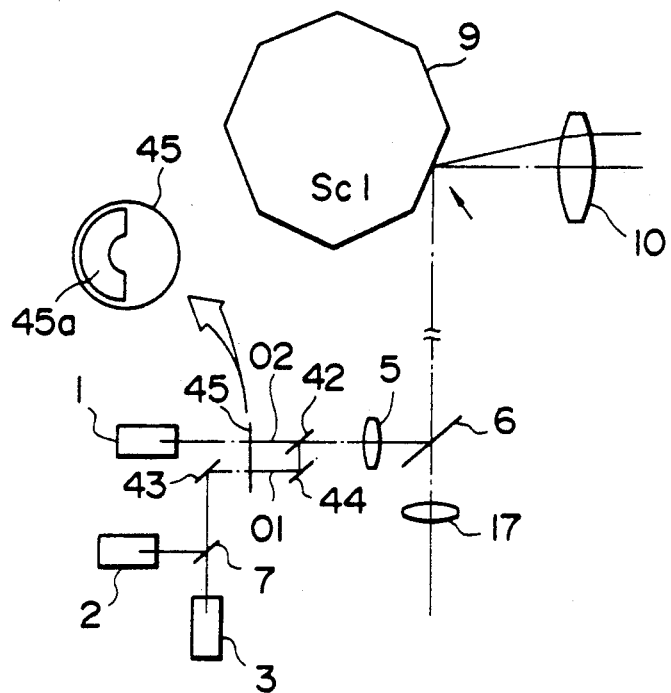
FIGS. 7 and 8 are arrangements showing another example of an optical path switch means shown in FIG. 1.

Also, as shown in FIG. 7, an embodiment may be designed such that a half mirror 42 is disposed between the lens 5 and the first laser 1, and two reflecting mirrors 43 and 44 are disposed between the dichroic mirror 7 and the half mirror 42, an optical path O1 between the reflecting mirrors 43 and 44 being parallel with an optical path O2 between the half mirror 42 and the first laser 1, a rotating plate 45, a half portion of which forms a light transmitting portion 45a, being disposed over the two optical paths O1 and O2, the rotating plate 45 being able to be rotated by 180°. In this case, the optical paths O1 and O2 can be switched by rotating the rotating plate 45 by 180°.

Figure 8:
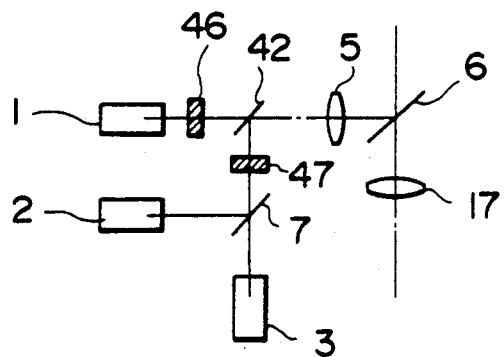

FIG. 8 may be designed as such that the rotating plate 45 and the two reflecting mirrors 43 and 44 of FIG. 7 are omitted, and high speed shutters 46 and 47 formed of a liquid crystal, or the like, are disposed between the half mirror 42 and the first laser 1, and between the dichroic mirror 7 and the half mirror 42 respectively.

As the present invention has been constructed as described above, there can be provided a laser scanning type eye fundus camera in which a retina color photographing can be performed in a shorter period of time than the conventional laser scanning type eye fundus camera and a clear color retina image can be obtained.

What I claim is:

1. A laser scanning type eye fundus camera comprising:

laser beam generating means for generating first, second, and third laser beams, each having a wavelength corresponding to one of the three primary colors;

a scanning optical system for scanning a laser beam over the retina of an eye to be tested;

switch means for selectively switching between a first group and a second group of the laser beams generated by said laser beam generating means and for guiding said selected group to said scanning optical system;

control means for controlling said switch means to selectively switch between said first group and said second group in synchronization with said scanning optical system to allow said scanning optical system to alternately scan one frame of the retina of the eye with said first group and one frame of the retina of the eye with said second group;

a light receiving optical system for guiding light reflected from the retina of the eye;

first light receiving means for receiving reflected light guided by said light receiving optical system from said first and said second laser beams;

second light receiving means for receiving reflected light guided by said light receiving optical system from said third laser beam; and image processing means for combining an output from said first and said second light receiving means to form a single color image of the retina.

2. A laser scanning type eye fundus camera according to claim 1, wherein said laser beam generating means comprises first, second, and third laser emitting elements adapted to emit laser beams with wavelengths corresponding to blue light, green light, and red light.

3. A laser scanning type eye fundus camera according to claim 1, wherein said switch means includes a quick return mirror disposed in an optical path of said scanning optical system.

4. A laser scanning type eye fundus camera according to claim 1, wherein said switch means comprises a rotating disc plate with a semicircular light transmitting portion.

5. A laser scanning type eye fundus camera according to claim 1, wherein said switch means comprises a liquid crystal shutter.

6. A laser scanning type eye fundus camera according to claim 2, wherein said first group comprises a laser beam with a wavelength corresponding to blue light and said second group comprises laser beams with wavelengths corresponding to green light and red light.

7. A laser scanning type eye fundus camera according to claim 1, wherein said first group comprises said first laser beam and said second group comprises said second and said third laser beams.

8. A laser scanning type eye fundus camera according to claim 7, wherein said first laser beam has a wavelength corresponding to blue light, said second laser beam has a wavelength corresponding to green light, and said third laser beam has a wavelength corresponding to red light.

9. A laser scanning type eye fundus camera according to claim 1, wherein said first group comprises said first and said third laser beams and said second group comprises said second and said third laser beams.

10. A laser scanning type eye fundus camera according to claim 9, wherein said first laser beam has a wavelength corresponding to blue light, said second laser beam has a wavelength corresponding to green light, and said third laser beam has a wavelength corresponding to red light.

11. A laser scanning type eye fundus camera according to claim 1, wherein said laser beam generating means comprises a dichroic mirror.

12. A laser scanning type eye fundus camera according to claim 1, wherein said light receiving optical system comprises a dichroic mirror.

* * * * *